(12) United States Patent
Ding et al.

(10) Patent No.: US 11,648,707 B2
(45) Date of Patent: May 16, 2023

(54) IN-SITU SQUARE SAMPLE ACQUISITION DEVICE AND METHOD FOR BOND CONTACT TEST OF SURROUNDING ROCK AND A SHOTCRETE LAYER

(71) Applicant: Changjiang River Scientific Research Institute, Changjiang Water Resources Commission, Hubei (CN)

(72) Inventors: Xiuli Ding, Hubei (CN); Shuling Huang, Hubei (CN); Yang Qin, Hubei (CN); Yuting Zhang, Hubei (CN); Zhiyang Gao, Hubei (CN); Dengxue Liu, Hubei (CN); Jun He, Hubei (CN)

(73) Assignee: Changjiang River Scientific Research Institute, Changjiang Water Resources Commission, Hubei (CN)

( * ) Notice: Subject to any disclaimer, the term of this patent is extended or adjusted under 35 U.S.C. 154(b) by 269 days.

(21) Appl. No.: 17/107,800

(22) Filed: Nov. 30, 2020

(65) Prior Publication Data
US 2022/0170825 A1    Jun. 2, 2022

(51) Int. Cl.
| | |
|---|---|
| *B28D 7/00* | (2006.01) |
| *G01N 1/08* | (2006.01) |
| *E21B 7/00* | (2006.01) |
| *G01N 33/24* | (2006.01) |
| *B23B 47/28* | (2006.01) |
| *E21B 49/02* | (2006.01) |
| *E21B 12/00* | (2006.01) |

(52) U.S. Cl.
CPC ............ *B28D 7/00* (2013.01); *E21B 7/001* (2013.01); *G01N 1/08* (2013.01); *B23B 47/28* (2013.01); *E21B 12/00* (2013.01); *E21B 49/02* (2013.01); *G01N 33/24* (2013.01)

(58) Field of Classification Search
CPC .. G01N 1/02; G01N 1/04; G01N 1/08; G01N 33/24; E21B 7/001; E21B 12/00; E21B 49/02; B23B 47/28; B28D 7/00
See application file for complete search history.

(56) References Cited

FOREIGN PATENT DOCUMENTS

CN         110987517 A  *  4/2020  ............... G01N 1/08

* cited by examiner

*Primary Examiner* — Benjamin R Schmitt
(74) *Attorney, Agent, or Firm* — Hickman Becker Bingham Ledesma LLP

(57) ABSTRACT

An in-situ square sample acquisition device and method for a bond contact test of a surrounding rock and a shotcrete layer are provided, the device includes a supporting shell, a fixing structure, hollow adjusting bolts and two borehole positioning frames, a guide hole is provided in a middle of the supporting shell, the frames are slidably fit in the guide hole, a plurality of positioning holes are provided in side walls of each of the frames, and the positioning holes in different frames are distributed in a staggered manner, four corners of the supporting shell are connected with four hollow adjusting bolts respectively, one end of each of the hollow adjusting bolts is fixedly provided with an adjusting nut, four fixing lugs are provided in four corners of each frame respectively, and the fixing structure includes four connecting bolts and four nuts.

10 Claims, 6 Drawing Sheets

IN-SITU SQUARE SAMPLE ACQUISITION DEVICE AND METHOD FOR BOND CONTACT TEST OF SURROUNDING ROCK AND A SHOTCRETE LAYER

TECHNICAL FIELD

The application relates to the technical field of geotechnical engineering test equipment, and in particular to an in-situ square sample acquisition device and method for a bond contact test of a surrounding rock and a shotcrete layer.

BACKGROUND

For geotechnical engineering, a field test and a laboratory test are necessary measures for engineering design and construction and science research. Compared with the field test, the laboratory test has advantages of facilitating a control of boundary conditions in the test, low economic cost and the like, and is a main measures for researching on a bond mechanical property between rock mass and the shotcrete layer. The bond mechanical property between the rock mass and the shotcrete layer can be effectively studied through the laboratory test, a bond strength between the rock mass and shotcrete layer is determined, which is of great significance for the geotechnical engineering design and construction and the scientific research.

A core sampling is a main measures for sampling in a bond test of the rock mass and shotcrete layer, but the core sampling is only suitable for drilling a cylindrical sample and a square sample cannot be obtained. In the case that the core sampling is applied to weak rock mass and there are weak cementing structural planes in the rock mass, in a drilling process of a drill bit, sawteeth at a front end of the drill bit cut and in turn apply a vibration load and a torsion load to the rock samples within the drill bit, and a hole wall of the drill bit also applies a torsion load to the rock samples within the drill bit during rotation of the drill bite, resulting in the rock samples in the drill bit broken at some weak cementing structural planes, thus it is difficult to sample dual mediums of the rock mass and the shotcrete layer, and a sampling rate is low.

SUMMARY

The embodiments aim to provide an in-situ square sample acquisition device and a method for a bond contact test of a surrounding rock and a shotcrete layer, which are used for solving the problems in the conventional art, reducing a disturbance to a sample during sampling and improving a success rate for sampling a square sample from dual mediums of the rock mass and shotcrete layer under a rock mass condition of a weak cementing structural plane.

The present disclosure provides an in-situ square sample acquisition device for a bond contact test of a surrounding rock and a shotcrete layer, which includes a supporting shell, a fixing structure, hollow adjusting bolts and two borehole positioning frames. The supporting shell and the borehole positioning frames both take a shape of square ring. A guide hole is provided in a middle of the supporting shell. The borehole positioning frames are slidably fit in the guide hole. Multiple positioning holes are provided in side walls of each of the borehole positioning frames. The positioning holes are through holes, and the positioning holes in different borehole positioning frames are distributed in a staggered mode. Four corners of the support shell are connected with four hollow adjusting bolts respectively, one end of each of the hollow adjusting bolts is fixedly provided with an adjusting nut. Four fixing lugs are provided in four corners of each borehole positioning frame respectively. The fixing structure includes four connecting bolts, a first end of each of the connecting bolts passes through respective one of the hollow adjusting bolts and is threadedly connected with an extension tube for self-tapping screw arranged in a rock wall, a second end of each of the connecting bolts passes through respective one of the fixing lugs and is threadedly connected with a nut. The respective fixing lugs correspond to the respective hollow adjusting bolts and the respective connecting bolts one to one. A fastening nut is firmly arranged on each of the connecting bolts, and the fastening nut is located between one of the borehole positioning frames and the supporting shell.

In some embodiments, a threaded hole may be provided in each of the four corners of the supporting shell, each threaded hole may correspond to one of the hollow adjusting bolts one to one, and each of the hollow adjusting bolts may be connected with respective threaded hole in a threaded manner.

In some embodiments, the supporting shell may be located between the fastening nut and the adjusting nut.

In some embodiments, one and only one borehole positioning frame may be connected with the connecting bolts.

In some embodiments, an axial direction of the positioning holes may be the same as an axial direction of the guide hole.

The present disclosure also provides an in-situ square sample acquisition method for a bond contact test of a surrounding rock and a shotcrete layer which is based on the above-mentioned in-situ square sample acquisition device for a bond contact test of a surrounding rock and a shotcrete layer and includes the following steps of:

(1) determining positions of four fixedly-mounting holes to be drilled on a surface of the rock wall to be sampled according to the threaded hole on each of the four corners of the supporting shell, drilling the fixedly-mounting holes by a handheld electric drill, and arranging the extension tube for self-tapping screw in each of the four fixed mounting holes;

(2) fixing the four hollow adjusting bolts in respective fixedly-mounting holes;

(3) connecting the four corners of the supporting shell with respective hollow adjusting bolts in a threaded manner, passing the first end of each of the four connecting bolts through respective one of the hollow adjusting bolts so as to be connected with the respective extension tube for self-tapping screw in a threaded manner, and fixing the supporting shell on the surface of the rock wall to be sampled by screwing the fastening nut;

(4) leveling and fastening the supporting shell by screwing the adjusting nut;

(5) sleeving four corners of a first borehole positioning frame of the two borehole positioning frames on the four connecting bolts respectively, mounting the nut on each of the connecting bolts so that each of the four fixed lugs of the first borehole positioning frame may be in close contact with the fastening nut and the first borehole positioning frame may be inserted into the guide hole of the supporting shell, and drilling a rock mass along a multiple positioning holes in the first borehole positioning frame by using a handheld electric drill;

(6) disassembling the first borehole positioning frame, sleeving four corners of a second borehole positioning frame of the two borehole positioning frames on the four connecting bolts respectively, mounting the nut on each of the connecting bolts so that each of the four fixed lugs of the second borehole positioning frame may be in close contact with the fastening nut, and the second borehole positioning frame may be inserted into the guide hole of the support shell; and (7) redrilling the rock mass along a plurality of positioning holes on the second borehole positioning frame by the handheld electric drill to realize a separation of a square rock sample from the rock mass under a condition of micro-disturbance.

Compared with the conventional art, the embodiments have the following technical effects.

The in-situ square sample acquisition device and the method for a bond contact test of a surrounding rock and a shotcrete layer of the embodiments have little disturbance to the sample when sampling, and improves the success rate for sampling the square sample from the double mediums of the rock mass and the shotcrete layer under the rock mass condition of the weak cementing structural plane.

BRIEF DESCRIPTION OF THE DRAWINGS

In order to more clearly illustrate the embodiments of the present disclosure, drawings used in the embodiments will be briefly described below. It is apparent that the drawings in the following description are only some embodiments of the present disclosure, and those skilled in the art can obtain other drawings according to the drawings without creative efforts.

Figure 1:
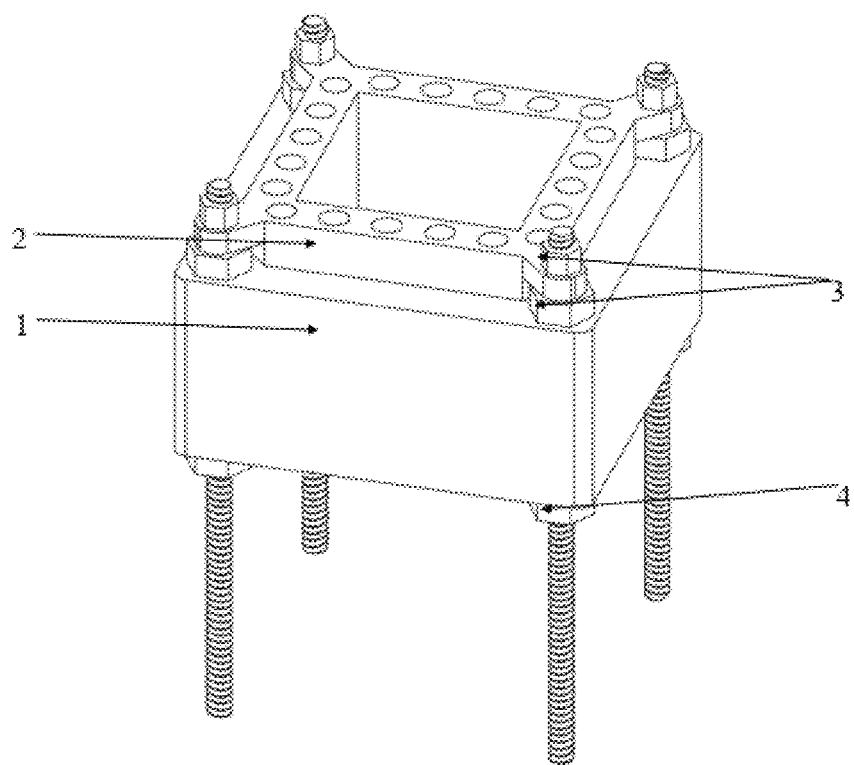
FIG. 1 is a first schematic structural diagram of an in-situ square sample acquisition device for a bond contact test of a surrounding rock and a shotcrete layer according to the present disclosure.
Figure 2:
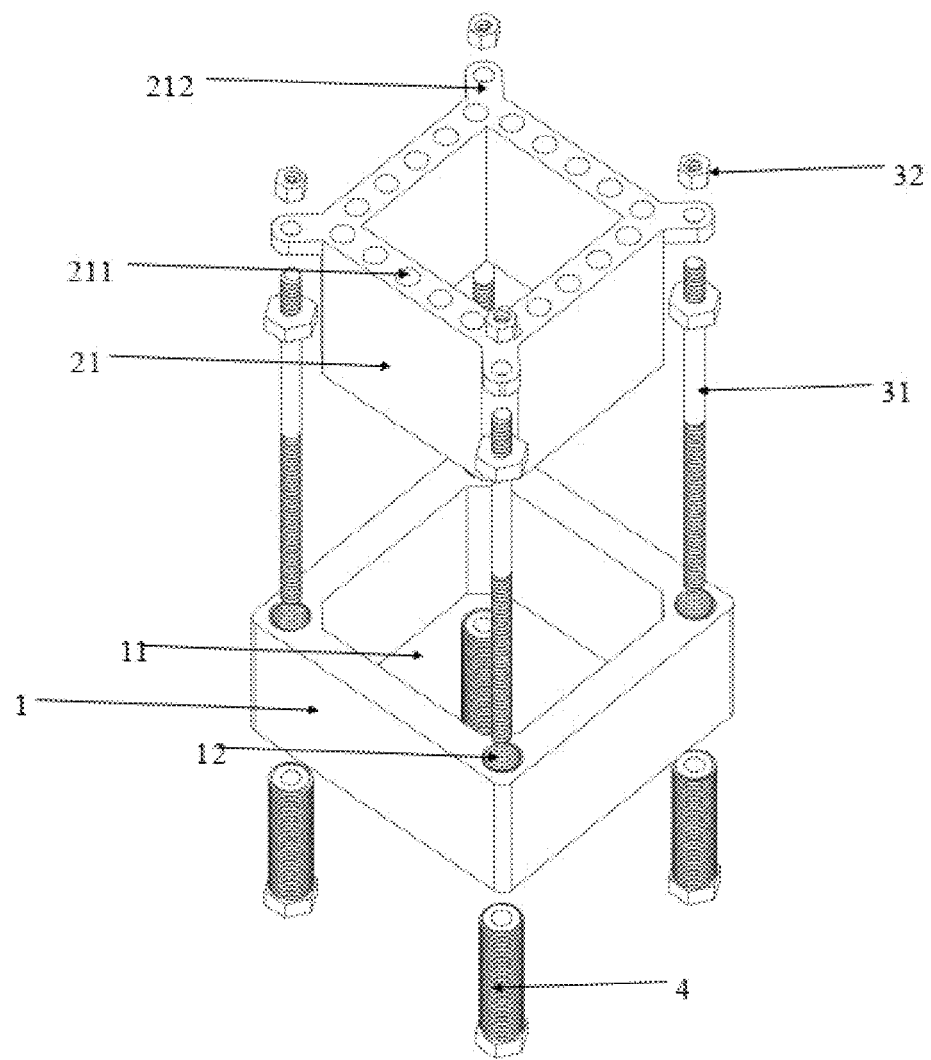
FIG. 2 is a second schematic structural diagram of the in-situ square sample acquisition device for the bond contact test of the surrounding rock and the shotcrete layer according to the present disclosure.
Figure 3:
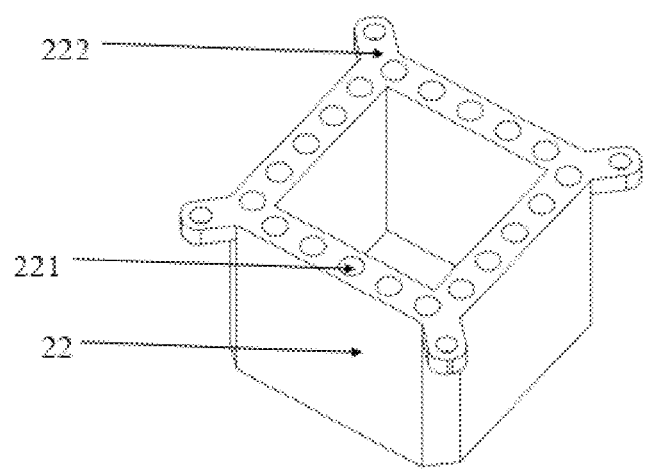
FIG. 3 is a schematic structural diagram of a second positioning member in the in-situ sample acquisition device for the bond contact test of the surrounding rock and the shotcrete layer according to the present disclosure.
Figure 4:
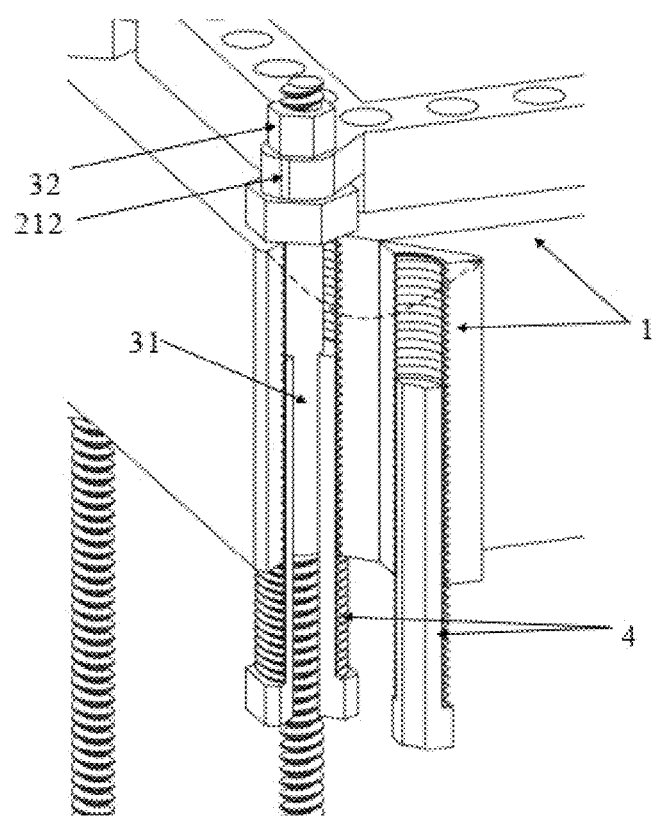
FIG. 4 is a schematic structural diagram of a part of the in-situ sample acquisition device for the bond contact test of the surrounding rock and the shotcrete layer according to the present disclosure.

List of the reference characters: 1 supporting housing; 2 borehole positioning frame; 3 fixing structure; 4 hollow adjusting bolt; 11 guide hole; 12 threaded hole; 21 first borehole positioning frame; 211 first positioning hole; 212 first fixing lug; 31 connecting bolt; 32 nut; 22 second borehole positioning frame; 221 second positioning hole; 222 second fixing lug; 51 first borehole; 52 second borehole; and 53 inscribed pattern.

DETAILED DESCRIPTION OF THE EMBODIMENTS

The technical solutions in the embodiments of the present disclosure will be clearly and completely described below with reference to the drawings in the embodiments of the present disclosure. It is apparent that the described embodiments are only a part of the embodiments of the present disclosure, and not all of the embodiments. All other embodiments, which can be obtained by a those skilled in the art without inventive effort based on the embodiments of the present disclosure, are within the scope of protection of the present disclosure.

The embodiments aim to provide an in-situ square sample acquisition device and a method for a bond contact test of a surrounding rock and a shotcrete layer, which are used for solving the problems in the conventional art, to reduce disturbance to a sample during sampling and improve a success rate for drilling and sampling a square sample from dual mediums of the rock mass and shotcrete layer under a rock mass condition of a weak cementing structural plane.

In order to make the above-mentioned objects, features and advantages of the present disclosure more comprehensible, the present disclosure is described in detail with reference to the accompanying drawings and particular embodiments.

As shown in FIGS. 1 to 6, an in-situ square sample acquisition device and a method for a bond contact test of a surrounding rock and a shotcrete layer of the embodiment includes a supporting shell 1, a fixing structure 3, hollow adjusting bolts 4 and two borehole positioning frames 2. The two borehole positioning frames 2 are a first borehole positioning frame 21 and a second borehole positioning frame 22 respectively. The supporting shell 1 and the borehole positioning frames 2 both take a shape of square ring. A guide hole 11 is provided in a middle of the supporting shell 1. The borehole positioning frames 2 may be slidably engaged with the guiding hole 11. Multiple positioning holes are provided in side walls of each borehole positioning frame, and the positioning holes are the through holes. The positioning holes in different borehole positioning frames 2 are distributed in a staggered mode.

Four corners of the supporting shell 1 each are provided with a threaded hole 12, respective threaded holes 12 correspond to respective hollow adjusting bolts one-to-one, and each hollow adjusting bolt 4 is connected with a corresponding threaded hole 12 in a threaded manner. A bottom of the hollow adjusting bolt is fixedly provided with an adjusting nut. A fixing lug is provided at each of four corners of each borehole positioning hole 2. The fixing structure 3 includes four connecting bolts 31 and four nuts 32, a first end of the connecting bolt 31 passes through corresponding hollow adjusting bolt 4 and is threadedly connected with an extension tube for self-tapping screw arranged in a rock wall. A fastening nut fixed on a screw rod of the connecting bolt 31 is sandwiched between the corner of the supporting shell 1 and the fixing lug of the borehole positioning hole 2. A second end of the connecting bolt 31 passes through a fixing lug and threadedly connected with the nut 32. Respective nuts 32 correspond to respective fixing lugs, respective connecting bolts 31, respective threaded holes 12 and respective hollow adjusting bolts 4 one to one.

It should be noted that the fastening nut is fixedly provided on the connecting bolt 31, the fastening nut is located between one borehole positioning frame 2 and the supporting shell 1, and the supporting shell 1 is located between the fastening nut and the adjusting nut. In the embodiment, two borehole positioning frames 2 are used alternately, and only one borehole positioning frame 2 is connected to the connecting bolt 31. And an axial direction of the positioning hole is the same as an axial direction of the guide hole 11.

The present disclosure also provides an in-situ square sample acquisition method for bond contact test of a surrounding rock and a shotcrete layer based on the above-mentioned in-situ square sample acquisition device for bond contact test of a surrounding rock and a shotcrete layer, which includes the following steps of:

(1) determining positions of four fixedly-mounting holes to be drilled on a surface of a rock wall to be sampled according to the threaded holes 12 on the four corners of the supporting shell 1, drilling the fixedly-mounting holes by a handheld electric drill and arranging the extension tube for self-tapping screw in the each of the four fixedly-mounting holes;

(2) connecting threaded holes 12 at four corners of the supporting shell 1 with respective hollow adjusting bolts 4 in a threaded manner, passing the first end of each of four connecting bolts 31 through respective hollow adjusting bolts 4 so as to be connected with the respective extension tube for self-tapping screw in a threaded manner;

(3) fixing the supporting shell 1 on the surface of the rock wall to be sampled by screwing the fastening nuts on the connecting bolts 31;

(4) leveling and fastening the supporting shell 1 by screwing the adjusting nuts at ends of the hollow adjusting bolts 4;

(5) sleeving four corners of a first borehole positioning frame 21 on four connecting bolts 31 respectively, then mounting nuts 32 on the connecting bolts 31 so that four first fixing lugs 212 of the first borehole positioning frame 21 are in close contact with the respective fastening nuts and the first borehole positioning frame 21 is inserted into the guide hole 11 of the supporting shell 1, and drilling the rock mass along multiple first positioning holes 211 by the handheld electric drill;

(6) disassembling the first borehole positioning frame 21, sleeving four corners of a second borehole positioning frame 22 on the four connecting bolts 31 respectively, and mounting nuts 32 on the connecting bolts 31 so that four second fixing lugs 222 of the second borehole positioning frame 22 are in close contact with the respective fastening nuts and the second borehole positioning frame 22 is inserted into the guide hole 11 of the supporting shell 1; and (7) redrilling the rock mass along multiple positioning holes 221 by the handheld electric drill.

Figure 5:
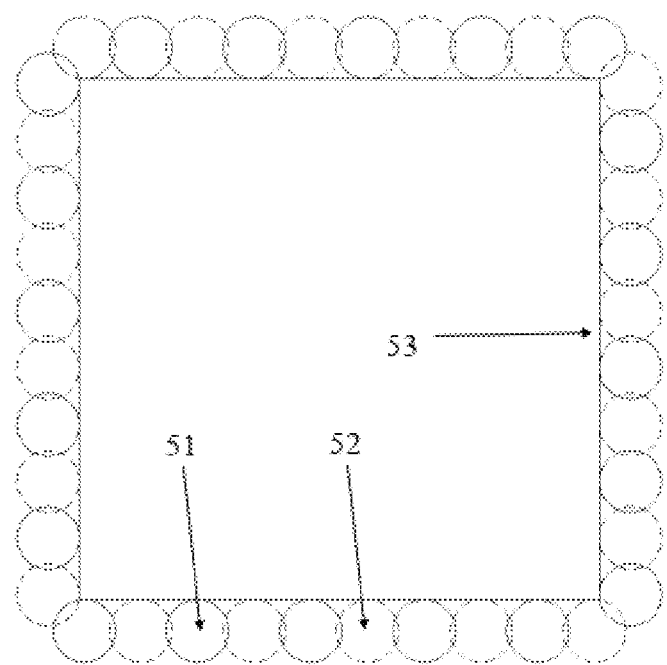
FIG. 5 is a diagram illustrating a distribution of boreholes and an inscribed pattern of the boreholes formed on a surface of a sample to be sampled after the in-situ sample acquisition device for the bond contact test of the surrounding rock and the shotcrete layer according to the present disclosure redrilled.
Figure 6:
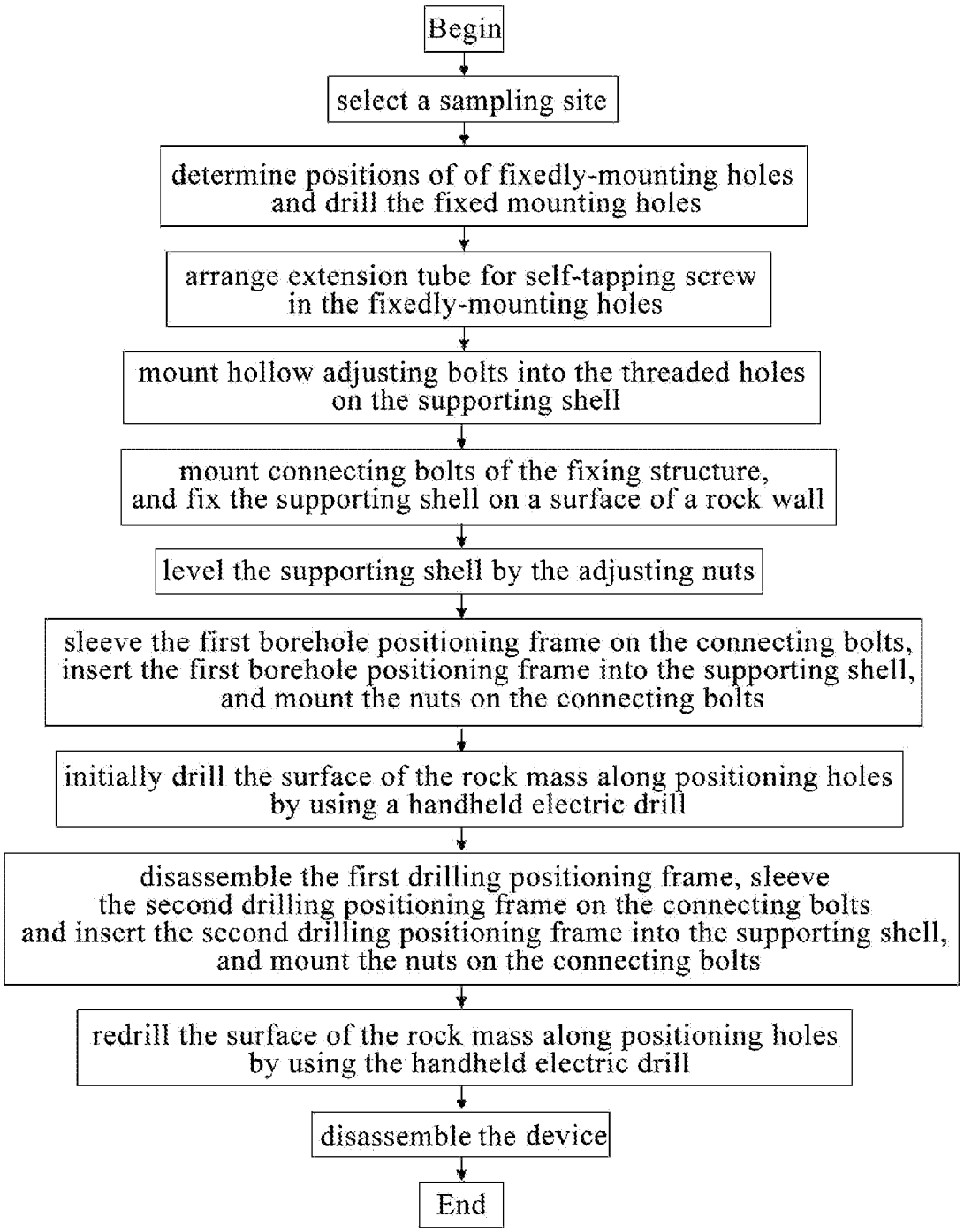
FIG. 6 is a flow chart of a method for obtaining the in-situ square sample of the bond contact test of the surrounding rock and the shotcrete layer.

Referring to FIG. 5, a first borehole 51 is a borehole formed in a surface of the sample to be sampled upon using the first borehole positioning frame 21 for drilling. A second borehole 52 is a borehole formed in the surface of the sample to be sampled upon using the second borehole positioning frame 22 for drilling. An inscribed pattern 53 is an inscribed pattern 53 of the borehole formed in the surface of the sample to be sampled after two borehole positioning frames 2 are used for redrilling. Thus, separating a square rock sample from the rock mass under a condition of micro-disturbance is realized.

It should be noted that in the description of the present disclosure, the terms such as "top", "bottom", "vertical", and "horizontal" indicating orientations or positional relationships represent orientations or positional relationships shown in the drawings, which are only for convenience in describing the present disclosure and simplifying the description, but do not indicate or imply that the device or element referred to must have a specific orientation, be constructed and operate in a specific orientation, and thus should not be construed as limiting the present disclosure. Furthermore, the terms "first", "second" and the like are used for descriptive purposes only and are not to be construed as indicating or implying relative importance.

The principle and the embodiments of the present disclosure are explained by using specific examples in the present specification, and the above description of the embodiments is only used to help understand the method and the techniques disclosed in the present disclosure; furthermore, for a person skilled in the art, according to the idea of the present disclosure, the specific embodiments and the application range may be changed. In summary, the description is not to be taken in a limiting sense.

What is claimed is:

1. An in-situ square sample acquisition device for a bond contact test of a surrounding rock and a shotcrete layer, comprising:
    a supporting shell;
    a fixing structure;
    hollow adjusting bolts; and
    two borehole positioning frames,
    wherein the supporting shell and the borehole positioning frames both take a shape of a square ring, a guide hole is provided in a middle of the supporting shell, the borehole positioning frames are slidably fit in the guide hole, a plurality of positioning holes are provided in side walls of each of the borehole positioning frames, the positioning holes are through holes, and the positioning holes in different borehole positioning frames are distributed in a staggered mode,
    wherein four corners of the support shell are connected with four hollow adjusting bolts respectively, one end of each of the hollow adjusting bolts is fixedly provided with an adjusting nut, four fixing lugs are provided in four corners of each of the borehole positioning frames respectively, the fixing structure comprises four connecting bolts, a first end of each of the connecting bolts passes through respective one of the hollow adjusting bolts and is threadedly connected with an extension tube for a self-tapping screw arranged in a rock wall, a second end of each of the connecting bolts passes through respective one of the fixing lugs and is threadedly connected with a nut, the respective fixing lugs correspond to the respective hollow adjusting bolts and the respective connecting bolts one to one, a fastening nut is firmly arranged on each of the connecting bolts, and the fastening nut is located between one of the borehole positioning frames and the supporting shell.

2. The in-situ square sample acquisition device for a bond contact test of a surrounding rock and a shotcrete layer according to claim 1, wherein a threaded hole is provided in each of the four corners of the supporting shell, each threaded hole corresponds to one of the hollow adjusting bolts one to one, and each of the hollow adjusting bolts is connected with respective threaded hole in a threaded manner.

3. The in-situ square sample acquisition device for a bond contact test of a surrounding rock and a shotcrete layer according to claim 1, wherein the supporting shell is located between the fastening nut and the adjusting nut.

4. The in-situ square sample acquisition device for a bond contact test of a surrounding rock and a shotcrete layer according to claim 1, wherein one and only one borehole positioning frame is connected with the connecting bolts.

5. The in-situ square sample acquisition device for a bond contact test of a surrounding rock and a shotcrete layer according to claim 1, wherein an axial direction of the positioning holes is the same as an axial direction of the guide hole.

6. An in-situ square sample acquisition method for a bond contact test of a surrounding rock and a shotcrete layer based on an in-situ square sample acquisition device for a bond contact test of a surrounding rock and a shotcrete layer, wherein the in-situ square sample acquisition device comprises a supporting shell, a fixing structure, hollow adjusting bolts and two borehole positioning frames, wherein the supporting shell and the borehole positioning frames both take a shape of a square ring, a guide hole is provided in a middle of the supporting shell, the borehole positioning frames are slidably fit in the guide hole, a plurality of positioning holes are provided in side walls of each of the borehole positioning frames, the positioning holes are through holes, and the positioning holes in different borehole positioning frames are distributed in a staggered mode, and wherein four corners of the support shell are connected with four hollow adjusting bolts respectively, one end of each of the hollow adjusting bolts is fixedly provided with an adjusting nut, four fixing lugs are provided in four corners of each of the borehole positioning frames respectively, the fixing structure comprises four connecting bolts, a first end of each of the connecting bolts passes through respective one of the hollow adjusting bolts and is threadedly connected with an extension tube for a self-tapping screw arranged in a rock wall, a second end of each of the connecting bolts passes through respective one of the fixing lugs and is threadedly connected with a nut, the respective fixing lugs correspond to the respective hollow adjusting bolts and the respective connecting bolts one to one, a fastening nut is firmly arranged on each of the connecting bolts, and the fastening nut is located between one of the borehole positioning frames and the supporting shell, the method comprising the following steps of:

(1) determining positions of four fixedly-mounting holes to be drilled on a surface of the rock wall to be sampled according to the threaded hole on each of the four corners of the supporting shell, drilling the fixedly-mounting holes by a handheld electric drill, and arranging the extension tube for the self-tapping screw in each of the four fixed mounting holes;

(2) fixing the four hollow adjusting bolts in respective fixedly-mounting holes;

(3) connecting the four corners of the supporting shell with respective hollow adjusting bolts in a threaded manner, passing the first end of each of the four connecting bolts through respective one of the hollow adjusting bolts so as to be connected with the respective extension tube for the self-tapping screw in a threaded manner, and fixing the supporting shell on the surface of the rock wall to be sampled by screwing the fastening nut;

(4) leveling and fastening the supporting shell by screwing the adjusting nut;

(5) sleeving four corners of a first borehole positioning frame of the two borehole positioning frames on the four connecting bolts respectively, mounting the nut on each of the connecting bolts so that each of four fixing lugs of the first borehole positioning frame is in close contact with the fastening nut and the first borehole positioning frame is inserted into the guide hole of the supporting shell, and drilling a rock mass along a plurality of positioning holes in the first borehole positioning frame by the handheld electric drill;

(6) disassembling the first borehole positioning frame, sleeving four corners of a second borehole positioning frame of the two borehole positioning frames on the four connecting bolts respectively, mounting the nut on each of the connecting bolts so that each of four fixing lugs of the second borehole positioning frame is in close contact with the fastening nut and the second borehole positioning frame is inserted into the guide hole of the supporting shell; and (7) redrilling the rock mass along a plurality of positioning holes on the second borehole positioning frame by the handheld electric drill to realize a separation of a square rock sample from the rock mass under a condition of micro-disturbance.

7. The in-situ square sample acquisition method for a bond contact test of a surrounding rock and a shotcrete layer according to claim 6, wherein a threaded hole is provided in each of the four corners of the supporting shell, each threaded hole corresponds to one of the hollow adjusting bolts one to one, and each of the hollow adjusting bolts is connected with respective threaded hole in a threaded manner.

8. The in-situ square sample acquisition method for a bond contact test of a surrounding rock and a shotcrete layer according to claim 6, wherein the supporting shell is located between the fastening nut and the adjusting nut.

9. The in-situ square sample acquisition method for a bond contact test of a surrounding rock and a shotcrete layer according to claim 6, wherein one and only one borehole positioning frame is connected with the connecting bolts.

10. The in-situ square sample acquisition method for a bond contact test of a surrounding rock and a shotcrete layer according to claim 6, wherein an axial direction of the positioning holes is the same as an axial direction of the guide hole.

* * * * *